United States Patent [19]
Hansen et al.

[11] Patent Number: 6,162,938
[45] Date of Patent: Dec. 19, 2000

[54] SECONDARY AMINE-FUNCTIONAL SILANES, SILANE-FUNCTIONAL POLYMERS THEREFROM, AND RESULTING CURED POLYMERS

[75] Inventors: Richard G. Hansen, Mahtomedi; Dean M. Moren, North St. Paul, both of Minn.

[73] Assignee: 3M Innovative Properties Company, St. Paul, Minn.

[21] Appl. No.: 09/196,276

[22] Filed: Nov. 19, 1998

[51] Int. Cl.$^7$ ...................................................... C07F 7/10
[52] U.S. Cl. .............................................................. 556/419
[58] Field of Search ............................................. 556/419

[56] References Cited

U.S. PATENT DOCUMENTS

| | | |
|---|---|---|
| 3,033,815 | 5/1962 | Pike et al. . |
| 3,627,722 | 12/1971 | Selter . |
| 3,632,557 | 1/1972 | Brode et al. . |
| 3,700,716 | 10/1972 | Berger et al. . |
| 3,759,968 | 9/1973 | Berger et al. . |
| 3,940,360 | 2/1976 | Carder . |
| 3,979,344 | 9/1976 | Bryant et al. . |
| 4,020,043 | 4/1977 | Siefken . |
| 4,067,844 | 1/1978 | Barron et al. . |
| 4,176,124 | 11/1979 | Darms et al. . |
| 4,209,455 | 6/1980 | Pepe . |
| 4,345,053 | 8/1982 | Rizk et al. . |
| 4,468,492 | 8/1984 | Piccirilli et al. . |
| 4,628,076 | 12/1986 | Chang et al. . |
| 4,718,944 | 1/1988 | Plueddemann . |
| 4,857,623 | 8/1989 | Emmerling et al. . |
| 5,095,045 | 3/1992 | Winkel et al. . |
| 5,118,290 | 6/1992 | Muller et al. . |
| 5,126,170 | 6/1992 | Zwiener et al. . |
| 5,174,813 | 12/1992 | Cifuentes et al. . |
| 5,189,190 | 2/1993 | Ching et al. . |
| 5,236,741 | 8/1993 | Zwiener et al. . |
| 5,260,467 | 11/1993 | Barnish et al. . |
| 5,364,955 | 11/1994 | Zwiener et al. . |
| 5,464,888 | 11/1995 | Owen . |
| 5,476,889 | 12/1995 | Owen . |
| 5,554,686 | 9/1996 | Frisch, Jr. et al. . |
| 5,587,502 | 12/1996 | Moren et al. . |
| 5,596,044 | 1/1997 | Gindin et al. . |
| 5,597,930 | 1/1997 | Wicks et al. . |
| 5,717,125 | 2/1998 | Wolter et al. . |
| 5,756,751 | 5/1998 | Schmalstieg et al. . |
| 5,955,561 | 9/1999 | Sundararaman ..................... 556/419 X |
| 5,990,333 | 11/1999 | Allen et al. ......................... 556/419 X |
| 6,020,448 | 2/2000 | Jenkner et al. ...................... 556/419 X |

FOREIGN PATENT DOCUMENTS

| | | |
|---|---|---|
| 0 210 444 A1 | 2/1987 | European Pat. Off. . |
| 0 459 304 A2 | 12/1991 | European Pat. Off. . |
| 0 831 108 A1 | 3/1998 | European Pat. Off. . |
| 295764 | 11/1971 | U.S.S.R. . |
| WO 98/18844 | 5/1998 | WIPO . |

*Primary Examiner*—Paul F. Shaver
*Attorney, Agent, or Firm*—Lisa M. McGeehan

[57] ABSTRACT

Secondary amine-functional silanes comprising at least one ester group and at least one amide group are disclosed. The secondary amine-functional silanes are preparable from relatively inexpensive, commercially available raw ingredients, are stable at room temperature and are reactive toward electrophiles. Also disclosed are silane-terminated polymers, silane-terminated polyurethane dispersions, and moisture-cured polymers derived therefrom.

21 Claims, No Drawings

SECONDARY AMINE-FUNCTIONAL SILANES, SILANE-FUNCTIONAL POLYMERS THEREFROM, AND RESULTING CURED POLYMERS

FIELD OF THE INVENTION

The invention relates generally to novel secondary amine-functional silanes, which have application in, for example, moisture-curable polymers, silane-terminated polymer dispersions, and cured polymers derived therefrom.

BACKGROUND OF THE INVENTION

Compounds containing more than one type of functional group are often referred to as multifunctional compounds. The type of functional groups determines the properties and applications of the compounds. When multifunctional compounds contain moisture-curable functional groups such as alkoxysilane groups, for example, the multifunctional compounds are useful in applications where polymer curing is effected by exposure of polymers containing the multifunctional compounds to moisture. Alkoxysilane groups can form siloxane (—Si—O—Si—) linkages in the presence of atmospheric moisture. Siloxane linkages not only form a polymer network, but they also improve adhesion of the polymers to non-porous surfaces, such as glass.

Multifunctional compounds containing moisture-curable functional groups have found use in many applications. For example, U.S. Pat. No. 5,587,502 describes the use of multifunctional compounds in the preparation of moisture-curable adhesives, sealants (e.g., automobile seam sealants), putties, and the like. The multifunctional compounds therein comprise both hydroxy and alkoxysilane moieties. The hydroxy functionality can react with isocyanate-functional materials to form alkoxysilane-functional polyurethanes. See also, PCT Publication No. WO98/18844, wherein multifunctional compounds comprising both hydroxy and alkoxysilane moieties are reacted with an isocyanate-functional poly(ether-urethane) to form an alkoxysilane-functional poly(ether-urethane). The cured compositions therefrom are also particularly useful as sealants.

U.S. Pat. No. 5,717,125 discloses a wide variety of multifunctional compounds that are both hydrolyzable and polymerizable to form both inorganic and organic networks, respectively, throughout the resulting composition. The compositions therein are purportedly particularly useful in dental applications. However, it is not always desirable to include polymerizable groups in the multifunctional compounds.

Multifunctional compounds bearing both amine and alkoxysilane moieties are well known. See, for example, U.S. Pat. Nos. 3,033,815; 3,627,722; 3,632,557; 3,700,716; 3,979,344; 4,067,844; 4,209,455; 4,628,076; 4,718,944; 4,857,623; 5,174,813; and 5,364,955. Both primary amine-functional alkoxysilanes and secondary amine-functional alkoxysilanes are described therein.

Primary amine-functional alkoxysilanes are often extremely reactive with a variety of electrophiles (e.g., isocyanates, oxirane rings, and anhydrides), resulting in strongly hydrogen-bonded products. For example, the reaction of primary amines with isocyanates is extremely fast and produces dihydrourea linkages. Dihydrourea linkages may disadvantageously increase product viscosities, however, which can hinder processability of the product, subsequent mobility of attached functional groups and reactivity of attached functional groups. Additionally, fast reaction rates, often associated with primary amine-functional alkoxysilanes, are undesirable in many applications. For example, uncontrollable reaction rates can lead to excessive generation of heat, fast gel times, and decreased reaction selectively.

In general, secondary amine-functional alkoxysilanes react more slowly with electrophiles than do the corresponding primary amine-functional alkoxysilanes. Furthermore, hydrogen bonding in their adducts is significantly reduced or eliminated. Examples of commercially available secondary amine-functional silanes include: 3-(N-phenyl) aminopropyltrimethoxysilane; 3-(N-methyl) aminopropyltrimethoxysilane; and 3,3'-iminobis (propyltrimethoxysilane). Methods of preparation are described in U.S. Pat. No. 3,632,557. However, costs of such secondary amine-functional alkoxysilanes, often twice those of their primary amine analogs, limit their commercial application.

U.S. Pat. Nos. 3,033,815 and 4,067,844 disclose secondary amine-functional alkoxysilanes that are formed by a Michael-type reaction of primary amine-functional alkoxysilanes with (meth)acrylate or (meth)acrylonitrile Michael-type receptors. Although these methods produce secondary amine-functional alkoxysilanes at relatively low cost, the reaction products are contaminated with varying quantities of primary and tertiary amine-functional alkoxysilanes.

Preparation of N-alkoxysilylalkyl-aspartic acid diesters from certain amino-alkyl alkoxysilanes and maleic or fumaric acid esters is disclosed in U.S. Pat. No. 5,364,955. These N-alkoxysilylalkyl-aspartic acid diesters react with isocyanates, however, to form polymers containing urea and ester groups. The polymers are reportedly unstable, however, with the urea groups cyclizing to hydantoins (See U.S. Pat. No. 5,756,71). This reaction is illustrated below, wherein X, Z, R, $R_2$, $R_3$, $R_4$, n, and m are as defined therein:

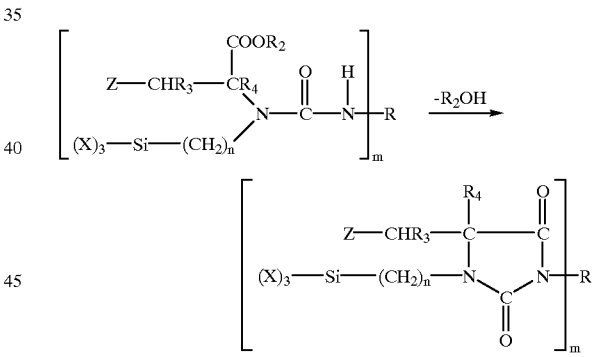

As can be seen from the reaction diagram, during cyclization, alcohol is expelled as a by-product. Expelled alcohol can be problematic since it may undesirably slow subsequent moisture-cure of the alkoxysilane moieties. Furthermore, hydantoin formation may lead to undesirable shrinkage of the resulting polymer. See also European Patent Application No. 0 831 108 A1, which discloses N-alkoxysilylalkyl-aspartic acid diesters and polyurethane products therefrom, which polyurethane products are reportedly useful as sealants.

While many multifunctional compounds, particularly secondary amine-functional silanes are known, a further variety of compounds would be desirable to enable tailorability for certain applications. For example, secondary amine-functional silanes that are stable without cyclizing to form hydantoins are desirable for use in applications where shrinkage, for example, from hydantoin formation is undesirable. One such application is the field of sealants, like automobile seam sealers. Furthermore, cost-effectiveness is also generally a consideration when selecting suitable multifunctional compounds for formulating compositions.

SUMMARY OF THE INVENTION

Secondary amine-functional silanes of the present invention are preparable at lower costs than many conventional secondary amine-functional silanes and resist hydantoin formation. Furthermore, methods for their preparation result in relatively pure reaction products. That is, other reaction products, such as primary or tertiary amine-functional silanes, for example, are minimized or eliminated.

In one embodiment, secondary amine-functional silanes of the present invention include chemical compositions of Formula I:

(I)

wherein:
X comprises at least one silane group; and
Y comprises a hydrocarbon backbone, at least one amide group on an α-carbon, and at least one ester group on a β-carbon with respect to N. In preferred embodiments, Y contains only one ester group and/or Y is ethylenically saturated. In a further embodiment, Y is ethylenically saturated and contains only one ester group.

A particularly preferred secondary amine-functional silane of the present invention corresponds to that of Formula II:

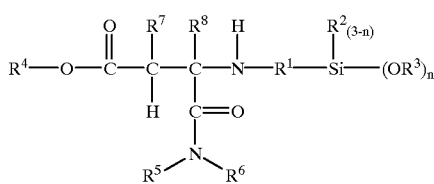
(II)

wherein:
n is 1, 2 or 3, preferably 3;
$R^1$ is a divalent linking group;
Each $R^2$ is independently a monovalent organic radical;
Each $R^3$ is independently a monovalent organic radical;
$R^4$ is a monovalent organic radical;
$R^5$ and $R^6$ are each independently selected from the group consisting of hydrogen and monovalent organic radicals or $R^5$ and $R^6$, when taken together, may form a 5- or 6-membered ring with the nitrogen atom;
$R^7$ is selected from the group consisting of hydrogen and monovalent organic radicals; and
$R^8$ is selected from the group consisting of hydrogen and monovalent organic radicals.

Preferably, $R^1$ is selected from the group consisting of linear and branched alkylene groups having 1 to about 6 carbon atoms. More preferably, $R^1$ is a propylene group.

Preferably, each $R^2$ is independently selected from the group consisting of linear and branched alkyl groups having 1 to about 6 carbon atoms. More preferably, each $R^2$ is independently selected from the group consisting of a methyl group and an ethyl group.

Preferably, each $R^3$ is independently selected from the group consisting of linear and branched alkyl groups having 1 to about 6 carbon atoms. More preferably, each $R^3$ is independently selected from the group consisting of a methyl group and an ethyl group.

Preferably, $R^4$ is an alkyl group having 1 to about 6 carbon atoms. More preferably, $R^4$ is selected from the group consisting of a methyl group and an ethyl group.

Preferably, $R^5$ is selected from the group consisting of hydrogen and alkyl groups having 1 to about 6 carbon atoms. More preferably, $R^5$ is hydrogen.

Preferably, $R^6$ is selected from the group consisting of an alkyl group having 1 to about 6 carbon atoms and an aryl group. More preferably, $R^6$ is an alkyl group.

Preferably, $R^7$ is selected from the group consisting of hydrogen and alkyl groups having 1 to about 6 carbon atoms. More preferably, $R^7$ is hydrogen.

Preferably, $R^8$ is selected from the group consisting of hydrogen and alkyl groups having 1 to about 6 carbon atoms. More preferably, $R^8$ is hydrogen.

The secondary amine-functional silanes are also useful for preparing moisture-curable silane-functional polymers derivable therefrom. Cured polymers are also derivable from such polymers.

In one embodiment, a moisture-curable silane-functional polymer corresponds to that of Formula III:

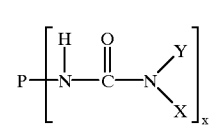
(III)

wherein P is an organic group having a molecular weight of at least about 15 and a valence of x, wherein x is an integer greater than or equal to 1. X and Y are as defined above.

In a particularly preferred embodiment, a moisture-curable silane-functional polymer corresponds to that of Formula IV:

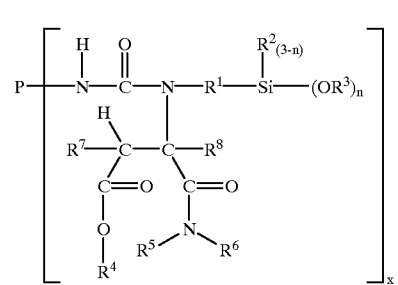
(IV)

wherein P is an organic group having a molecular weight of at least about 15 and a valence of x, wherein x is an integer greater than or equal to 1. $R^1$–$R^8$ and n are as defined above.

The secondary amine-functional silanes are also useful for preparing silane-terminated polyurethane dispersions derivable therefrom. Cured polymers are derivable from such dispersions.

Secondary amine-functional silanes of the present invention and polymers therefrom are useful in preparing composites and other articles. For example, composites comprise a substrate and a layer of moisture-curable silane-functional polymer coated thereon. The polymers can be cured to provide composites comprising a substrate and a layer of cured polymer derived from the moisture-curable silane-functional polymer coated thereon. The secondary amine-functional silanes are also particularly useful for forming coatings, adhesives, elastomers, and sealants, such as automobile seam sealants.

Also disclosed is a method of preparing secondary amine-functional silanes of the present invention. The method comprises the step of reacting a primary amine-functional silane having the structure:

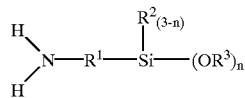

with one or more amide-ester Michael-type receptors having the structure:

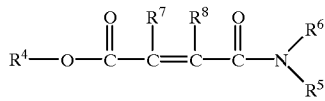

wherein:
n is 1, 2 or 3;
$R^1$ is a divalent linking group;
Each $R^2$ is independently a monovalent organic radical;
Each $R^3$ is independently a monovalent organic radical;
$R^4$ is a monovalent organic radical;
$R^5$ and $R^6$ are each independently selected from the group consisting of hydrogen and monovalent organic radicals or $R^5$ and $R^6$, when taken together, may form a 5- or 6-membered ring with the nitrogen atom;
$R^7$ is selected from the group consisting of hydrogen and monovalent organic radicals; and
$R^8$ is selected from the group consisting of hydrogen and monovalent organic radicals.

DETAILED DESCRIPTION OF THE PREFERRED EMBODIMENTS

In general, secondary amine-functional silanes of the present invention comprise an ester group and an amide group. The secondary amine-functional silanes can be represented by Formula I:

(I)

wherein:
X contains at least one silane group; and
Y comprises a hydrocarbon backbone, at least one amide group on an α-carbon, and at least one ester group on a β-carbon with respect to N. As understood by one of ordinary skill in the art, the α-carbon atom is the first carbon adjacent N and the β-carbon atom is the second carbon adjacent N.

In a preferred embodiment, the ester group is a terminal group of the hydrocarbon backbone. It is believed that increasing the distance between the amine and ester groups also minimizes and typically prevents hydantoin formation or subsequent cyclization.

In another preferred embodiment, Y contains only one ester group. By reducing the number of ester groups in the multifunctional compound, hydantoin formation or subsequent cyclization is even further minimized or eliminated.

In yet another preferred embodiment, Y is ethylenically saturated. As such, the secondary amine-functional silane does not contain polymerizable groups, which polymerizable groups may not be desirable for certain applications.

Most preferably, Y contains only one ester group and Y is ethylenically saturated. For example, preferred secondary amine-functional silanes of the invention are those of Formula II:

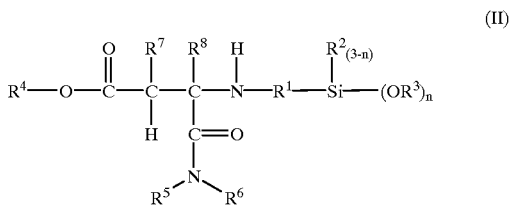

(II)

wherein:
n is 1, 2 or 3;
$R^1$ is a divalent linking group;
Each $R^2$ is independently a monovalent organic radical;
Each $R^3$ is independently a monovalent organic radical;
$R^4$ is a monovalent organic radical;
$R^5$ and $R^6$ are each independently selected from the group consisting of hydrogen and monovalent organic radicals or $R^5$ and $R^6$, when taken together, may form a 5- or 6-membered ring with the nitrogen atom;
$R^7$ is hydrogen or a monovalent organic radical; and
$R^8$ is hydrogen or a monovalent organic radical.

It is believed that the structure of Y minimizes and typically prevents hydantoin formation or subsequent cyclization.

Monovalent organic radicals include, for example, hydrocarbon groups (e.g., linear or branched alkyl groups, alkenyl groups, cycloalkyl groups, or aryl groups) that may, optionally, contain one or more heteroatoms (e.g., oxygen, nitrogen, sulfur, silicon, and the like), functional groups (e.g., carbonyl groups, halo groups, nitro groups, cyano groups, alkoxy groups, thio groups, amino groups, ester groups, aryl groups, silane groups, and the like), or combinations thereof. Typical monovalent organic radicals include hydrocarbon groups having from about 1 to about 20 carbon atoms, preferably from about 1 to about 12 carbon atoms, more preferably from about 1 to about 8 carbon atoms.

Divalent linking groups can be, for example, linear or branched hydrocarbon groups. Typical divalent linking groups include hydrocarbon groups having from 1 to about 20 carbon atoms, preferably from about 1 to about 12 carbon atoms, more preferably from about 1 to about 8 carbon atoms, optionally containing one or more heteroatoms (e.g., oxygen, nitrogen, sulfur, silicon, and the like), functional groups (e.g., carbonyl groups, halo groups, nitro groups, cyano groups, alkoxy groups, thio groups, amino groups, ester groups, aryl groups, silane groups, and the like), or combinations thereof.

Particularly preferred compounds of Formula II are those embodiments wherein:
$R^1$ is a linear or branched alkylene group having 1 to about 6 carbon atoms, more preferably a propylene group;
Each $R^2$ is independently a linear or branched alkyl group having 1 to about 6 carbon atoms, more preferably a methyl group or an ethyl group;

Each $R^3$ is independently a linear or branched alkyl group having 1 to about 6 carbon atoms, more preferably a methyl group or an ethyl group;

$R^4$ is an alkyl group of 1 to about 6 carbon atoms, more preferably a methyl group or an ethyl group;

$R^5$ is hydrogen or an alkyl group of 1 to about 6 carbon atoms, more preferably hydrogen;

$R^6$ is an alkyl group of 1 to about 6 carbon atoms or an aryl group, more preferably an alkyl group, for example t-butyl;

$R^7$ is hydrogen or an alkyl group of 1 to about 6 carbon atoms, more preferably hydrogen;

$R^8$ is hydrogen or an alkyl group of 1 to about 6 carbon atoms, more preferably hydrogen; and n is 2 or 3, more preferably 3.

Secondary Amine-Functional Silane Synthesis

The secondary amine-functional silanes of the invention may be formed by any suitable method. Preferably, due to the relatively lower cost thereof, the secondary amine-functional silanes are prepared by reaction of one or more primary amine-functional silanes with various amide-esters. For example, the secondary amine-functional silanes are preparable by reacting primary amine-functional silanes having the structure:

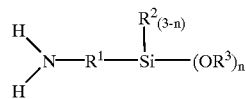

wherein $R^1$, $R^2$, $R^3$, and n are as defined above, with one or more amide-ester Michael-type receptors having the structure:

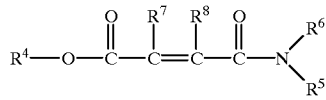

wherein $R^4$–$R^8$ are as defined above.

The amide-ester Michael-type receptors may be formed by any of a number of suitable methods. Useful amide-ester Michael-type receptors include, for example, adducts of alcohols with isomaleimides. The use of an organotin salt as a catalyst may increase the yield of such a reaction. For example, the reaction of an isomaleimide with an alcohol can be carried out at from about 0° C. to about 100° C., preferably from about 22° C. to about 70° C. Examples of organotin salts useful as catalysts include: dibutyltin laurate, dibutyltin diacetate, dimethyltin dilaurate, stannous octoate, bis(lauryldibutyltin)oxide, and dibutyltin dimercaptide. A preferred catalyst is dibutyltin diacetate. The amount of catalyst used may vary from about 0.1 to about 10 mol % based on the amount of alcohol.

An alternate method of preparing amide-ester Michael-type receptors includes reacting maleic anhydride with an amine followed by converting the resulting carboxylic acid group to an ester. These methods are described in co-pending U.S. patent application having Ser. No. 09/109,588. Other methods are readily recognizable by those of ordinary skill in the art.

Any suitable primary amine-functional silane may be used in the preferred method. Many primary amine-functional silanes are commercially available and are relatively inexpensive raw materials. Useful primary amine-functional silanes include, for example, 3-aminopropyltriethoxysilane; 3-aminopropyltrimethoxysilane; 3-(2-aminoethyl)aminopropyltrimethoxysilane; 3-aminopropylmethyldiethoxysilane; 3-aminopropyltris(2-(2-methoxyethoxy)ethoxy)silane; 3-aminopropyltriisopropenyloxysilane; 3-aminopropyltri(butanone oximo)silane; 4-aminobutyltriethoxysilane; N-2-(aminoethyl)-3-aminopropyltris(2-ethylhexoxy)silane; 3-aminopropyldimethylethoxysilane; 3-aminopropyldiisopropylethoxysilane; and 3-aminopropylphenyldiethoxysilane. 3-aminopropyltriethoxysilane and 3-aminopropyltrimethoxysilane are preferred.

The reaction of a primary amine-functional silane with an amide-ester Michael-type receptor is often spontaneous, rapid, and nearly quantitative. Accordingly, the secondary amine-functional silanes may be synthesized, for example, by simply allowing mixtures of primary amine-functional silanes and amide-ester Michael-type receptors to stand overnight at 70° C. in the absence of catalyst.

The reaction generally proceeds to 95–99% completion within about 24 hours. Hydrogen, carbon, and silicon nuclear magnetic resonance spectroscopy ($^1$H-NMR, $^{13}$C-NMR, and $^{29}$Si-NMR, respectively) are useful in confirming structures of the reaction products. Since the reactions are essentially clean (i.e., the reaction products include less than about 5 weight % products other than secondary amine-functional silanes, typically essentially no products other than secondary amine-functional silanes), purification of the reaction products is generally not required, which may be advantageous for certain applications.

Polymers Derived from Secondary Amine-Functional Silanes

The secondary amine-functional silane compounds of the present invention can be reacted with other compounds. For example, the secondary amine-functional silane compounds can be reacted with compounds having electrophilic groups. Such electrophilic groups include, for example, isocyanate groups, oxirane rings, and anhydride groups. Included within the scope of this invention are silane-functional polymers obtained by reacting the secondary amine-functional silanes with organic groups reactive therewith. These silane-functional polymers are then moisture-curable to form a polymer network containing siloxane linkages.

Preferably, the secondary amine-functional silane compounds are reacted with compounds containing at least one isocyanate group. As such, a preferred silane-functional polymer resulting therefrom has the following structure:

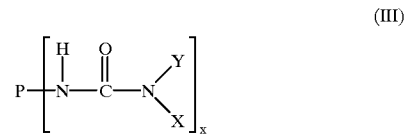

(III)

wherein X and Y are as defined with respect to Formula I. P is an organic group, such as, for example, a polyurethane, preferably having a molecular weight of at least about 15, more preferably about 84–20,000, even more preferably about 3,000–12,000, and a valence of x, wherein x is an integer greater than or equal to 1.

In a more preferred embodiment, a silane-functional polymer of the present invention corresponds to that of Formula IV:

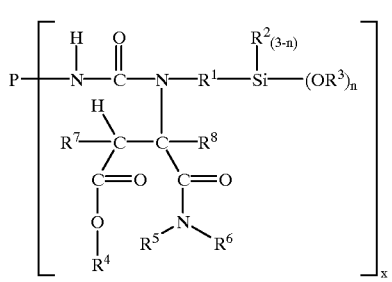

wherein n and $R^1$–$R^8$ are as defined with respect to Formula II. P is an organic group, such as, for example, a polyurethane, preferably having a molecular weight of at least about 15, more preferably about 84–20,000, even more preferably about 3,000–12,000, and a valence of x, wherein x is an integer greater than or equal to 1.

To form the polymers, an organic group reactive with the secondary amine-functional silanes of the present invention is allowed to react as such. Typically such reactive organic groups contain at least one electrophilic group (e.g., an isocyanate group or an anhydride group).

For example, isocyanate-functional prepolymers (e.g., polyurethanes having reactive isocyanate groups) are reactive with the secondary amine-functional silanes. Such isocyanate-functional prepolymers may be prepared by means well known to those of ordinary skill in the art. These isocyanate-functional prepolymers can then be reacted with secondary amine-functional silanes (with or without a catalyst), as is known in the art. The ingredients are typically allowed to react at temperatures of about 25° C. to about 90° C.

In a particularly preferred embodiment, the secondary amine-functional silanes are reacted with isocyanate-terminated polyurethane prepolymers. Resulting aminosilane-terminated polymers comprise polyurethane urea segments end-capped with aminosilane groups. The isocyanate-terminated polyurethane prepolymers are prepared by any suitable method, as well known to those of ordinary skill in the art.

In a further embodiment, the secondary amine-functional silanes are useful in preparing silane-terminated polyurethane dispersions. In general, the silane-terminated polyurethane dispersions are prepared by first forming a polyurethane prepolymer by combining a polyisocyanate component with isocyanate reactive compounds. This prepolymer is then dispersed in a water phase that typically provides chain extension and silane termination of the polyurethane prepolymer. In this manner, the polyurethane prepolymer can be end-capped, chain-extended, and dispersed in a water phase.

A summary of basic polymer chemistry and technology which explains and summarizes these reactions and processes as they relate to polyurethanes can be found, for example, in *Polyurethanes: Chemistry and Technology,* Saunders and Frisch, Interscience Publishers (New York, 1963 (Part I) and 1964 (Part II)). The isocyanate-functional prepolymers may be prepared using a wide range of isocyanate equivalent to hydroxyl equivalent ratios (NCO:OH). Preferred NCO:OH ratios are about 1.25:1 to about 2:1.

While solventless methods of preparation and use may be preferred, the silane-functional polymers may be prepared in and/or used with solvent. For example, solvents such as acetone, butanone, ethyl acetate, toluene, naphtha, N-methylpyrrolidinone, N, N-dimethylformamide, acetonitrile, tetrahydrofuran, and ethylene glycol dimethyl ether can be used for such methods.

The silane-functional polymers may be utilized in the form of a composite and, optionally, in the presence of various additives including moisture-curable catalysts, plasticizers, thixotropic agents, biocides, adhesion promoters, corrosion inhibitors, pigments, fillers, colorants, photostabilizers, antioxidants, perfumes, and other suitable additives.

Useful moisture-curable catalysts include, for example: metal salts and complexes, amines, organic acids, and inorganic acids. Specific examples of useful moisture-curable catalysts include: dibutyltin diacetylacetonate; tetraisopropyl titanate; calcium oxide; N,N,N',N'-tetramethylguanidine; tetrabutylammonium hydroxide; trifluoroacetic acid; dibutyl phosphate; dibutyltin dimethoxide; and 1,3-diazabicycloundec-7-ene.

Useful plasticizers include, for example: benzoates, adipates, phthalates, sebacates, and phosphates. The plasticizers may be present in any suitable amount, although it is generally preferred that the amount of plasticizer not exceed 50% by weight based on total weight of the composition. Specific examples of useful plasticizers include: diisodecyl phthalate, N-ethyl-o, p-toluenesulfonamide, butyl benzyl phthalate, and dipropylene glycol dibenzoate.

Useful thixotropic, or antisagging, agents include, for example: castor waxes, fumed silicas, treated clays, and polyamides. Preferably, the thixotropic agent is essentially non-reactive with the silane functionalities to minimize shelf-life problems.

Useful adhesion promoters include, for example, various silanes, such as those available under the tradenames SILQUEST A-1120, SILQUEST A-187, and SILQUEST A-189 (commercially available from Witco; Endicott, N.Y.).

Fillers may be added to alter, for example, the color, rheology, and ultimate mechanical properties of the silane-functional polymer. Types and use of fillers are well known to those of ordinary skill in the art. Examples of useful fillers: include calcium carbonate, titanium dioxide, carbon black, iron oxide, talc, ceramic microspheres and clay. Ground and/or precipitated calcium carbonates are preferred fillers in applications where low cost and opacity are desirable.

Useful antioxidants and photostabilizers include, for example, those commercially available under the tradenames TINUVIN 770, TINUVIN 327, TINUVIN 1130, and TINUVIN 292 (commercially available from Ciba, Hawthorne, N.Y.). Hindered phenols (e.g., those comprising 2,6-di-tert-butylphenol residues) and hindered amines (e.g., those comprising 2,2,6,6-tetramethylpiperidine residues) are particularly preferred antioxidants.

More than one type of silane-functional polymer may be blended together for certain applications. For example, moisture-curing kinetics of compositions derived from the present silane-functional polymers may be more readily controlled by utilizing various blends of silane-functional polymers. For example, a preferred blend comprises triethoxysilane-functional polymers and trimethoxysilane-functional polymers.

As noted above, silane-functional polymers of the present invention are moisture-curable and provide polymer networks containing siloxane linkages upon curing. Such cured polymers of the present invention have a wide variety of utilities. For example, the polymers are useful in the preparation of coatings, adhesives, sealants, and elastomers.

In one particular application, silane-functional polymers of the present invention are useful as sealants (e.g., automotive seam sealers) for the automotive industry. Automotive seam sealers are typically used in high temperature environments, and as a result, must exhibit thermal stability. In addition, they are typically required to adhere to a wide variety of surfaces, such as cold-rolled steel, primed steel, and galvanized steel. Furthermore, they are typically required to accept paint shortly after application, while still wet, drying to a cured film essentially free of defects (e.g., bubbles or shrinkage that can be measured by the unaided human eye). Due to the minimization or reduction of hydantoin formation in secondary amine-functional silanes of the present invention, shrinkage of the sealants is advantageously minimized. As such, the present secondary amine-functional silanes and polymers derived therefrom are particularly advantageous for use in automobile seam sealers.

Those of ordinary skill in the art can appreciate how to formulate such sealants. For example, a preferred automobile seam sealer contains about 100 parts by weight of a silane-functional polymer; about 5 to about 200 parts by weight of at least one plasticizer; about 1 to about 10 parts by weight of at least one antioxidant; about 0.1 to about 5 parts by weight of at least one moisture-curable catalyst; about 0.1 to about 10 parts by weight of at least one adhesion promoter; about 0.1 to about 10 parts by weight of at least one dehydrator; about 0 to about 500 parts by weight of at least one filler; and about 0 to about 20 parts by weight of at least one thixotropic agent.

Automotive seam sealers typically comprise additives such as those listed above. When the sealer is used in area of the automobile that will be exposed to high temperatures, a combination of two antioxidants comprising a hindered phenolic antioxidant such as those available under the trade designation, BHT (commercially available from Aldrich Chemical, Milwaukee, Wis.) and a hindered amine light stabilizer such as those available under the trade designation, TINUVIN 770 (commercially available from Ciba, Hawthorne, N.Y.) is preferably used. In this embodiment, the weight ratio of hindered amine light stabilizer to hindered phenolic antioxidant is preferably about 1:4.

The secondary amine-functional silanes, dispersions, polymers, and articles therefrom are exemplified in the following examples. These examples are merely for illustrative purposes only and are not meant to be limiting on the scope of the appended claims. All parts, percentages, ratios, etc. in the examples and the rest of the specification are by weight unless indicated otherwise.

EXAMPLES

| Abbreviation or Trade Designation | Description |
| --- | --- |
| A-171 | A trimethoxyvinylsilane commercially available from Witco; Endicott, NY under the trade designation SILQUEST A-171 |
| A-1100 | 3-aminopropyltriethoxysilane, commercially available from Witco; Endicott, NY under the trade designation SILQUEST A-1100 |
| A-1110 | 3-aminopropyltrimethoxysilane, commercially available from Witco; Endicott, NY under the trade designation SILQUEST A-1110 |
| A-1120 | N-beta(aminoethyl) gamma-aminopropyltrimethoxysilane commercially available from Witco; Endicott, NY under the trade designation SILQUEST A-1120 |
| D1110 | N-methylaminopropyltrimethoxysilane, commercially available from United Chemical Technology, Bristol, PA |
| DESMODUR 1 | Isophorone diisocyanate, commercially available from Bayer Corp., Pittsburg, PA under the trade designation DESMODUR 1 |
| DIDP | A diisodecyl phthalate plasticizer, commercially available from Exxon, Houston, TX |
| DISPARLON 6500 | A polyamide thixotropic agent commercially available from King Industries, Norwalk, CT |
| DMPA | 2,2-bis(hydroxymethyl)propionic acid, commercially from Aldrich Chemical, Milwaukee, WI |
| ELFTEX-8 | A carbon black filler commercially available from Cabot, Inc., Boston, MA |
| IRGANOX 1010 | An antioxidant commercially available from Ciba, Hawthorne, NY |
| ISOPAR H | An aliphatic hydrocarbon solvent commercially available from Exxon, Houston, TX |
| NEOSTANN U220 | Dibutyltin diacetylacetonate commerically available from Keneka, New York, NY |
| NMP | 1-methyl-2-pyrrolidinone commercially available from Aldrich Chemical, Milwaukee, WI |
| PFINYL 402 | A calcium carbonate commercially available from Specialty Mineral, Adams, MA |
| PPG 3025 | 3,000 molecular weight polypropylene glycol, commercially available from ARCO Chemical; Newtown Square, PA |
| RITCIZER-8 | N-ethyl-o, p-toluenesulfonamide plasticizer, commercially available Rit-Chem Co. Inc., Pleasantville, NY |
| SAS | A secondary amine-functional silane prepared according to Example 1 (SAS-1) or Example 2 (SAS-2) |
| STPUU | A silane-terminated polyurethane urea polymer prepared according to Example 3 (STPUU-1) or Example 4 (STPUU-2) |
| T-1 | Dibutyltin diacetate, commercially available from Air Products; Allentown, PA under the trade designation DABCO T-1 |
| T-12 | Dibutyltin dilaurate, commercially available from Air Products, Allentown, PA under the trade designation DABCO T-12 |
| TBIMI | tert-butylisomaleimide, (5-(tert-butylamino)-2,5-dihydro-2-furanone) prepared according to Example 1, infra |
| TINUVIN 770 | A photostabilizer commercially available from Ciba, Hawthorne, NY |
| TONE 0240 | A caprolactone-based polyol commercially available from Union Carbide, Danbury, CT |
| ULTRAPFLEX | A calcium carbonate commercially available from Specialty Mineral, Adams, CT |
| Y-9020 | N-butylaminopropyltrimethoxysilane, commercially available from Witco, Endicott, NY under the trade designation SILQUEST Y-9020 |
| Y-9669 | N-phenylaminopropyltrimethoxysilane, commercially available from Witco, Endicott, NY under the trade designation SILQUEST Y-9669 |

Example 1

Preparation of SAS-1

Part I: Preparation of (Z)-4-(tert-butylamino)-4-oxo-2-butenoic acid

In a round-bottom flask with a nitrogen atmosphere and containing a mechanical stirrer, a thermometer and an addition funnel, was combined 1,073 grams (10.9 moles) of maleic anhydride (commercially available from Aldrich Chemical, Milwaukee, Wis.) and 6,062 grams of acetonitrile. The mixture was stirred to dissolve the solids and cooled to −7° C. To this was slowly added 800 grams, (10.9 moles) of tert-butylamine (commercially available from Aldrich Chemical, Milwaukee, Wis.) at a rate such that the temperature remained below 0° C. (approximately 2.5 hour addition time). The mixture was stirred at −7° C. for one hour and then overnight at room temperature. The solid was collected by filtration, washed with 500 milliliters acetonitrile and dried to give 1,355 grams of (Z)-4-(tert-butylamino)-4-oxo-2-butenoic acid as a white solid. $^{13}$C NMR indicated the product to be 94.62 weight % (Z)-4-(tert-butylamino)-4-oxo-2-butenoic acid, and 5.38 weight % tert-butylamine. This material was used without further purification for the next reaction.

Part II: Preparation of 5-(tert-butylimino)-2,5-dihydro-2-furanone

In a round bottom flask with a nitrogen atmosphere and containing a mechanical stirrer, a thermometer, an addition funnel and a condenser, was combined 700 grams (4.0 moles) of (Z)-4-(tert-butylamino)-4-oxo-2-butenoic acid and 7,757 grams dichloromethane. The mixture was cooled to −5° C. and 439 grams (4.0 moles) ethyl chloroformate (commercially available from Aldrich Chemical, Milwaukee, Wis.) was added. The mixture was cooled to −10° C. and 409 grams (4.0 moles) triethylamine (commercially available from Aldrich Chemical, Milwaukee, Wis.) was added slowly at a rate such that the temperature remained below −7° C. Stirring was continued at −5° C. for 2.5 hours during which time the evolution of carbon dioxide was observed. The mixture was warmed to 11° C. and a premix of 272 grams of sodium bicarbonate dissolved in 3,640 grams of distilled water was added. The mixture was stirred for 10 minutes, allowed to phase separate, and the aqueous phase was removed. The organic phase was extracted three times, each time with 3 liters of distilled water. The organic phase was dried with 275 grams of sodium sulfate, filtered and the solvent was removed in vacuo at 30° C. The residue was purified by distillation (50° C., 0.05 millimeters of Hg) to give 550 grams of 5-(tert-butylimino)-2,5-dihydro-2-furanone. This material is hereinafter referred to as TBIMI (tert-butylisomaleimide). $^{13}$C NMR indicated the product to be >99% pure.

Part III: Preparation of Amide-Methylester

A mixture of 0.209 gram (6.52 milliequivalents) of anhydrous methanol (commercially available from Aldrich Chemical, Milwaukee, Wis.) and 0.004 gram of T-1 was prepared and mixed for approximately 5 minutes. To this mixture was added 1.000 gram (6.53 milliequivalents) TBIMI and the resulting mixture was mixed for 2 days under ambient conditions. The product solidified upon cessation of mixing to form a white crystalline solid. $^1$H-NMR indicated a purity of >99% of the male(amide-ester) product.

Part IV: Preparation of SAS-1

A sample of 0.808 gram (4.36 milliequivalents) of the amide-ester of Part III was placed in a 70° C. oven for 10–15 minutes until melted. To this was added 0.782 gram (4.36 milliequivalents) A-1110 and the mixture was mixed for 10 minutes. The reaction mixture was placed in a 70° C. oven for 24 hours. The product was a clear, very slightly yellow liquid. $^1$H-NMR indicated a purity of 95% of the secondary aminosilane product.

Example 2

Preparation of SAS-2

Parts I & II
Same as Example 1

Part III: Preparation of the Amide-Ethylester

A mixture of 0.308 gram (6.68 milliequivalents) of absolute (200 proof) ethanol (commercially available from AAPER Chemical, Shelbyville, Ky.) and 0.005 gram of T-1 was prepared and mixed for approximately 5 minutes. To this mixture was added 1.024 grams (6.68 milliequivalents) TBIMI. The resulting composition was mixed for 2 days under ambient conditions. The product solidified upon cessation of mixing to form a white crystalline solid. $^1$H-NMR indicated a purity of >99.7% of the male(amide-ester) product.

Part IV: Preparation of SAS-2

A sample of 0.808 gram (4.05 milliequivalents) of the amide-ester of Part III was placed in a 70° C. oven for 10–15 minutes until melted. To this was added 0.898 gram (4.06 milliequivalents) A-1100 and the mixture was mixed for 10 minutes. The reaction mixture was placed in a 70° C. oven for 24 hours. The product was a clear, very slightly yellow liquid. $^1$H-NMR indicated a purity of 97% of the secondary aminosilane product.

Example 3

Preparation of STPUU-1

Part I: Preparation of Polyurethane Prepolymer

In a flask, 917.00 grams (0.5997 OH equivalents) of PPG 3025, 100.00 grams (0.8997 NCO equivalents) of DESMODUR I, and 2.00 grams T-12 were combined and heated to 70° C. under a nitrogen atmosphere for 6 hours.

Part II: Preparation of STPUU-1

In a flask, 102.50 grams (0.281 NH equivalents) of SAS-1 and 954.00 grams (0.281 NCO equivalents) of the prepolymer from Part I were combined (no noticeable exotherm occurred) and mixed for 45 minutes at ambient temperature. The mixture was subsequently heated to 70° C. for 16 hours. STPUU-1 appeared as a clear, slightly yellow liquid with a room temperature Brookfield viscosity of 6,200 Pascal seconds.

Example 4

Preparation of STPUU-2

Part I: Preparation of Polyurethane Prepolymer
Same as Example 3

Part II: Preparation of STPUU-2

In a flask, 113.70 grams (0.270 NH equivalents) of SAS-2 and 916.50 grams (0.270 NCO equivalents) of the prepolymer from Part I were combined (no noticeable exotherm occurred) and mixed for 45 minutes at ambient temperature. The mixture was subsequently heated to 70° C. for 16 hours. STPUU-2 appeared as a clear, slightly yellow liquid with a room temperature Brookfield viscosity of 5,100 Pascal seconds.

Examples 5–7

Formulation of Silane-Terminated Polyurethanes

Example 5

In a one-quart can, 10.62 weight % (based on total weight of the formulation) STPUU-1 and 10.62 weight % STPUU-2 were combined with 7.72 weight % DIDP, 1.93 weight % RITCIZER-8, 0.21 weight % TINUVIN 770, 0.85 weight % IRGANOX 1010 and 0.01 weight % ELFFEX-8 and the mixture was stirred under nitrogen with low shear for 5 minutes. 0.58 weight % DISPARLON 6500 was then added and mixing was continued for an additional 10 minutes under nitrogen with high shear. 40.54 weight % PFINYL 402 and 18.34 weight % ULTRAPFLEX were added with continued high shear mixing under nitrogen for 30 minutes and the batch temperature was maintained between 88° C. and 93° C. The batch temperature was then reduced to 50°

C.–55° C. and a solution containing 3.61 weight % ISOPAR H, 0.87 weight % A-171, and 0.02 weight % T-12 were added and the batch temperature was maintained at 50° C.–55° C. for 60 minutes under nitrogen. A solution containing 2.55 weight % NMP and 0.42 weight % NEOSTANN U220 was added to the batch along with 1.06 weight % A-1120 and the batch was mixed for 15 minutes at high shear under nitrogen to completely disperse the catalyst. The batch was then removed from the mixer and degassed with slow stirring under a vacuum of 28–30 millimeters of Hg for 5 minutes. The finished product was transferred to cartridges and placed in a desiccator until tested.

Example 6

In a quart can, 21.24 weight % STPUU-2 (based on total weight of the formulation) was combined with 7.72 weight % DIDP, 1.93 weight % RITCIZER-8, 0.21 weight % TINUVIN 770, 0.85 weight % IRGANOX 1010 and 0.01 weight % ELFTEX-8 and the mixture was stirred under nitrogen with low shear for 5 minutes. 0.58 weight % DISPARLON 6500 was then added and mixing was continued for an additional 10 minutes under nitrogen with high shear. 40.54 weight % PFINYL 402 and 18.34 weight % ULTRAPFLEX were added with continued high shear mixing under nitrogen for 30 minutes and the batch temperature was maintained between 88° C. and 93° C. The batch temperature was then reduced to 50° C.–55° C. and a solution containing 3.61 weight % ISOPAR H, 0.87 weight % A-171, and 0.02 weight % T-12 were added and the batch temperature was maintained at 50° C.–55° C. for 60 minutes under nitrogen. A solution containing 2.55 weight % NMP and 0.42 weight % NEOSTANN U220 was added to the batch along with 1.06 weight % A-1120 and the batch was mixed for 15 minutes at high shear under nitrogen to completely disperse the catalyst. The batch was then removed from the mixer and degassed with slow stirring under a vacuum of 28–30 millimeters of Hg for 5 minutes. The finished product was transferred to cartridges and placed in a desiccator until tested.

Example 7

In a quart can, 5.31 weight % STPUU-1 (based on total weight of the formulation) and 15.93 weight % STPUU-2 were combined with 7.72 weight % DIDP, 1.93 weight % RITCIZER-8, 0.21 weight % TINUVIN 770, 0.85 weight % IRGANOX 1010 and 0.01 weight % ELFTEX-8 and the mixture was stirred under nitrogen with low shear for 5 minutes. 0.58 weight % DISPARLON 6500 was then added and mixing was continued for an additional 10 minutes under nitrogen with high shear. 40.54 weight % PFINYL 402 and 18.34 weight % ULTRAPFLEX were added with continued high shear mixing under nitrogen for 30 minutes and the batch temperature was maintained between 88° C. and 93° C. The batch temperature was then reduced to 50° C.–55° C. and a solution containing 3.61 weight % ISOPAR H, 0.87 weight % A-171, and 0.02 weight % T-12 were added and the batch temperature was maintained at 50° C.–55° C. for 60 minutes under nitrogen. A solution containing 2.55 weight % NMP and 0.42 weight % NEOSTANN U220 was added to the batch along with 1.06 weight % A-1120 and the batch was mixed for 15 minutes at high shear under nitrogen to completely disperse the catalyst. The batch was then removed from the mixer and degassed with slow stirring under a vacuum of 28–30 millimeters of Hg for 5 minutes. The finished product was transferred to cartridges and placed in a desiccator until tested.

Testing of Examples 5–7

Test Methods

Tack Free Time

This test was performed in a controlled environment having a temperature of about 21° C. and a relative humidity of about 50%. An approximately 0.6-centimeter-diameter bead of the moisture-curable formulation was applied to the test surface. Tack free time was the time required to produce a surface on the bead which could be lightly touched with a wooden applicator stick without transfer to the wooden applicator stick.

Sag

An approximately 0.6-centimeter-diameter, 23-centimeter-long bead of the moisture-curable formulation was applied to a horizontal cold-rolled steel panel. The panel was then vertically inclined such that the length of the bead was in a horizontal position and the flow of the bead down the panel (in millimeters) was measured.

Caulk Rate

Caulk rate was measured through an approximately 0.6-millimeter-diameter orifice at 345 kilopascals (50 psi) pressure using an air gun.

Viscosity

Viscosities were determined at 22° C. using a Brookfield DV-1+ viscometer with a #7 spindle (spindle speed in revolutions per minute is noted in the table for each sample) and are reported in Pascal seconds (Pa sec).

Hardness

This test was performed in a controlled environment having a temperature of about 21° C. and a relative humidity of about 50%. An approximately 0.6-centimeter-diameter bead of the moisture-curable formulation was dispensed onto a cold-rolled steel panel. The hardness of the bead was measured after 24 hours (initial reading) and after 7 days (final reading) using a SHORE DUROMETER Type A hardness tester.

Adhesion

An approximately 0.6-centimeter-diameter, 23-centimeter-long bead of the moisture-curable formulation was applied to a cold-rolled steel panel that had been cleaned by wiping first with methyl ethyl ketone, then with toluene, and then again with methyl ethyl ketone. The bead was allowed to cure for one week in a controlled environment having a temperature of about 21° C. and a relative humidity of about 50%. One end of the bead was cut away from the steel panel to form a free end. The free end was pulled, and the failure mode was noted. Cohesive failure occurred when the cured formulation split leaving residue on the panel. Adhesive failure occurred when the cured formulation lifted off the panel, leaving no residue. Of these two modes of failure, cohesive failure is preferred for automotive sealants.

Cold Flexibility

A panel bearing a bead of cured moisture-curable formulation composition was prepared as described according to the adhesion test method above. The panel was held at approximately −34° C. for one hour. The panel was then quickly bent 180° approximately halfway along the length of the bead over a 2.54-centimeter-diameter rod such that the cured formulation was positioned along the outside radius. The formulation failed this test if it showed cracks visible to the unaided human eye at the point of bending. The adhesion failure mode, as described for the adhesion test, was also measured after the cold flexibility test was performed.

Cure-Through

This test was performed in a controlled environment having a temperature of about 21° C. and a relative humidity of about 50%. Cure-through was determined as the depth of cure (in millimeters) after a given interval of time at 21° C./50% relative humidity. For testing, an uncured sealant was placed in an apparatus having a channel with dimension of 20 millimeters in width and 305 millimeters in length. The depth of the channel gradually varied from about 0 millimeters at a first end to about 13 millimeters at a second end. The sealant was allowed to at least partially cure. After a given time interval (as noted in the Table 2), the cured sealant was pulled back from the first end of the channel until uncured material was seen in the bottom of the channel. A horizontal distance along the channel was measured in millimeters from the point of origin (i.e., where channel depth is about 0 millimeters). The horizontal distance was divided by 23.5 (slope of the channel) to obtain the cure depth.

Paint Adhesion Test

An approximately 0.6-centimeter-diameter, 23-centimeter-long bead of the moisture-curable formulation was applied to a cold-rolled steel panel that had been cleaned by wiping first with methyl ethyl ketone, then with toluene, and then again with methyl ethyl ketone. The bead was then smoothed to form an approximately 0.3-centimeter-thick film.

Paint (PPG DELTRON base/CONCEPT clear paint, obtained from Pittsburgh Plate Glass Co.; Strongsville, Ohio) was applied to separate films of the moisture-curable formulations after the films had aged for 1 hour, 1 day or 3 days. The painting sequence was per the manufacturer instructions: one part base coat (DBU 9700, obtained from Pittsburgh Plate Glass Co.; Strongsville, Ohio) was mixed with 1.5 parts reducer (DRR 1170, obtained from Pittsburgh Plate Glass Co.; Strongsville, Ohio). Two applications of base coat were applied fifteen minutes apart using a spray pressure of 310 kilopascals. Twenty minutes later, two coats of the clear coat (comprising 2 parts clear (DCU 2020, obtained from Pittsburgh Plate Glass Co.; Strongsville, Ohio), 1 part hardener (DU 5, obtained from Pittsburgh Plate Glass Co.; Strongsville, Ohio), and 1 part reducer (DT 870, obtained from Pittsburgh Plate Glass Co.; Strongsville, Ohio)) were applied to the base coat, the second coat being applied 15 minutes after the first coat, using a spray pressure of 310 kilopascals. The resulting laminates comprising the substrate, moisture-curable sealant composition, and paint were allowed to age for 3 days.

The paint adhesion of the moisture-curable formulations of the invention were then measured using ASTM D 3359-90. Thus the test specimen was crosshatched with a razor, adhesive tape (232 masking tape or SCOTCH 898 filament tape, commercially available from Minnesota Mining and Manufacturing Co., St. Paul, Minn.) was applied and then withdrawn in peel mode. Table 3 reports the percentage of paint removed for samples prepared from Example 5. Along with the percentage removed are reported corresponding values from ASTM D 3359-90.

Results

TABLE 1

| Ex. | Tack Free Time (min) | Sag (mm) | Caulk Rate (g/min) | Viscosity-Pa sec (spindle speed in rpm) | 24 Hour Shore A Hardness | 7 Day Shore A Hardness | Failure Mode* | Cold Flex | Failure Mode after Cold Flex* |
|---|---|---|---|---|---|---|---|---|---|
| 5 | 9 | 0 | 2,365 | 99,600 (2) 18,800 (20) | 32 | 56 | C | Pass | C |
| 6 | >45 | 0 | 4,651 | 83,200 (2) 14,600 (20) | 20 | 55 | C | Pass | C |
| 7 | 12 | 0 | 2,651 | 106,800 (2) 19,500 (20) | 29 | 55 | C | Pass | C |

*C equals cohesive failure

TABLE 2

| Ex. | 24 Hour Cure Through (mm) | 48 Hour Cure Through (mm) | 7 Day Cure Through (mm) |
|---|---|---|---|
| 5 | 3.0 | 4.1 | 7.5 |
| 6 | 2.5 | 3.7 | 6.8 |
| 7 | 2.7 | 3.7 | 7.0 |

TABLE 3

Paint Adhesion for Example 5

| Time Aged Prior To Paint Application | Masking Tape Rating-ASTM D3359-90 (% Paint Removed) | Filament Tape Rating-ASTM D3359-90 (% Paint Removed) |
|---|---|---|
| 1 hour | 5B (0%) | 5B (0%) |
| 1 day | 5B (0%) | 5B (0)% |
| 3 days | 5B (0%) | 5B (0)% |

Example 8, Comparative Examples 1A–D

Preparation of Silane-Terminated Urethane Dispersions

Example 8

Part I: Preparation of Prepolyme

In a flask with a nitrogen atmosphere and equipped with a heating mantel, condenser, mechanical stirrer, and a thermometer fitted with a temperature controller was placed 279.15 grams (2.5112 equivalents) of DESMODUR I, 682.94 grams (0.6890 equivalents) of TONE 0240, 37.91 grams (0.5650 equivalents) of DMPA, and 250.00 grams of NMP. The stirred mixture was heated to 40–50° C. To this was added 0.20 gram of T-12 and the resulting stirred mixture was heated to 80° C. for 2 hours.

Part II: Preparation of a Urethane Dispersion

A premix was made with 292.00 grams of distilled water, 3.92 grams of triethylamine (commercially available from Aldrich Chemical, Milwaukee, Wis.), 4.46 grams (0.149 equivalents) of ethylene diamine (commercially available from Aldrich Chemical, Milwaukee, Wis.) and 6.77 grams (0.0186 equivalents) of SAS-1 (Example 1). The premix was added to the holding tank of a homogenizer (Model HC-8000, commercially available from Microfluidics Corp., Newton, Mass.) and allowed to circulate. 170.15 grams (0.1711 equivalents) of the urethane prepolymer from Part I was added over 10 minutes to the homogenizer at an air line pressure of 621 kilopascals. A stable dispersion was formed.

Comparative Example 1A

Part I: Preparation of a Urethane Prepolymer
  Same as Example 8
Part II: Preparation of a Urethane Dispersion A premix was made with 292.00 grams of distilled water, 3.92 grams of triethylamine (commercially available from Aldrich Chemical, Milwaukee, Wis.), 4.46 grams (0.149 equivalents) of ethylene diamine (commercially available from Aldrich Chemical, Milwaukee, Wis.) and 3.33 grams (0.0186 equivalents) of A-1110. The premix was added to the holding tank of a homogenizer (Model HC-8000, commercially available from Microfluidics Corp., Newton, Mass.) and allowed to circulate. 170.15 grams (0.1711 equivalents) of the urethane prepolymer from Part I was added over 10 minutes to the homogenizer at an air line pressure of 621 kilopascals. A stable dispersion was formed.

Comparative Example 1B

Part I: Preparation of a Urethane Prepolymer
  Same as Example 8
Part II: Preparation of a Urethane Dispersion A premix was made with 292.00 grams of distilled water, 3.92 grams of triethylamine (commercially available from Aldrich Chemical, Milwaukee, Wis.), 4.46 grams (0.149 equivalents) of ethylene diamine (commercially available from Aldrich Chemical, Milwaukee, Wis.) and 3.55 grams (0.0186 equivalents) of D-1110. The premix was added to the holding tank of a homogenizer (Model HC-8000, commercially available from Microfluidics Corp., Newton, Mass.) and allowed to circulate. 170.15 grams (0.1711 equivalents) of the urethane prepolymer from Part I was added over 10 minutes to the homogenizer at an air line pressure of 621 kilopascals. A stable dispersion was formed.

Comparative Example 1C

Part I: Preparation of a Urethane Prepolymer
  Same as Example 8
Part II: Preparation of a Urethane Dispersion A premix was made with 292.00 grams of distilled water, 3.92 grams of triethylamine (commercially available from Aldrich Chemical, Milwaukee, Wis.), 4.46 grams (0.149 equivalents) of ethylene diamine (commercially available from Aldrich Chemical, Milwaukee, Wis.) and 4.33 grams (0.0186 equivalents) of Y-9020. The premix was added to the holding tank of a homogenizer (Model HC-8000, commercially available from Microfluidics Corp., Newton, Mass.) and allowed to circulate. 170.15 grams (0.1711 equivalents) of the urethane prepolymer from Part I was added over 10 minutes to the homogenizer at an air line pressure of 621 kilopascals. A stable dispersion was formed.

Comparative Example 1D

Part I: Preparation of a Urethane Prepolymer
  Same as Example 8
Part II: Preparation of a Urethane Dispersion A premix was made with 292 grams of distilled water, 3.92 grams of triethylamine (commercially available from Aldrich Chemical, Milwaukee, Wis.), 4.46 grams (0.1486 equivalents) of ethylene diamine (commercially available from Aldrich Chemical, Milwaukee, Wis.) and 4.33 grams (0.0186 equivalents) of Y-9669. The premix was added to the holding tank of a homogenizer (Model HC-8000, commercially available from Microfluidics Corp., Newton, Mass.) and allowed to circulate. 170.15 grams (0.1711 equivalents) of the urethane prepolymer from Part I was added over 10 minutes to the homogenizer at an air line pressure of 621 kilopascals. A stable dispersion was formed.

Testing of Example 8, Comparative Examples 1A–1D

Test Methods

Film Preparation

For testing, films of the compositions of Example 8 and Comparative Examples 1A–1D were prepared as follows. A 6-inch by 8-inch (2.2 centimeters by 15.2 centimeters) aluminum panel coated with a polytetrafluoroethylene tape was used to create a dam. The dam was created by surrounding the perimeter of the panel with a 1-centimeter-wide by 0.12-centimeter-thick tape. The panel and surrounding dam were filled with the appropriate dispersion and allowed to cure at room temperature and about 50% relative humidity.

Water Absorption

Samples (5 small pieces) were cut out of the films that had been dried and allowed to cure for 1, 2, 3, 4 or 5 days at room temperature. These samples were weighed and placed in a jar containing sufficient water to cover all of the sample pieces and the jar was sealed. After 1 week at room temperature, the samples were removed, dabbed dry with a paper towel to remove excess water from the surface of the sample, and reweighed. From the sample weight and the weight gained by the sample, the % by weight of water absorbed by the sample was calculated. The % water absorbed was equal to:

(Weight of Wet Sample–Weight of Dry Sample)/Weight of Dry Sample.

Mechanical Properties

Mechanical testing (tensile and elongation) was performed on a SINTECH Model 10 tensile tester (commercially available from Sintech, Stoughton, Mass.). Testing was performed according to ASTM Test Method D 412-98a, except size of dumbbell-shaped specimens therein was modified per dimensions below. Samples were prepared according to Method A (dumbbell-shaped and straight specimens) films prepared from the dispersion and were dried and allowed to cure for 1, 2, 3, 4 or 5 days at room temperature. Dumbbell-shaped specimens, approximately 0.318 centimeters in width and approximately 0.159 centimeters in thickness, were tested at a crosshead speed of 5.08 centimeters/minute (2.0 inches/minute).

Results

Table 4 contains water absorption data for samples cured for different lengths of time. Table 5 contains percent elongation data for samples cured for different lengths of time. Table 6 contains tensile strength data for samples cured for different lengths of time.

TABLE 4

| | Water Absorption (% by weight) | | | | |
|---|---|---|---|---|---|
| | Cure Time (Days at Room Temperature) | | | | |
| Ex. | 1 | 2 | 3 | 4 | 5 |
| 8 | 0.0 | 0.0 | 0.0 | 0.0 | 0.0 |
| C-1A | 10.0 | 11.3 | 11.7 | 10.0 | 10.9 |
| C-1B | 12.5 | 7.1 | 7.9 | 7.4 | 7.8 |
| C-1C | 2.7 | 3.6 | 3.5 | 2.0 | 2.4 |
| C-1D | 9.9 | 7.9 | 8.1 | 6.4 | 5.5 |

TABLE 5

| | Elongation (%) | | | | |
| --- | --- | --- | --- | --- | --- |
| | Cure Time (Days at Room Temperature) | | | | |
| Ex. | 1 | 2 | 3 | 4 | 5 |
| 8 | 1,440 | 1,103 | 1,096 | 1,044 | 786 |
| C-1A | 720 | 1,034 | 953 | 1,046 | 955 |
| C-1B | 1,053 | 987 | 1,072 | 1,197 | 979 |
| C-1C | 852 | 880 | 1,061 | 1,041 | 881 |
| C-1D | 973 | 1,173 | 1,051 | 1,292 | 1,060 |

TABLE 6

| | Tensile Strength (kilopascals) | | | | |
| --- | --- | --- | --- | --- | --- |
| | Cure Time (Days at Room Temperature) | | | | |
| Ex. | 1 | 2 | 3 | 4 | 5 |
| 8 | 2,217 | 9,329 | 15,086 | 23,767 | 22,257 |
| C-1A | 1,197 | 7,771 | 14,555 | 18,561 | 19,430 |
| C-1B | 1,911 | 6,491 | 9,818 | 14,342 | 16,292 |
| C-1C | 704 | 11,184 | 11,549 | 13,018 | 14,293 |
| C-1D | 1,502 | 7,357 | 10,363 | 16,789 | 15,886 |

Various modifications and alterations of the invention will become apparent to those skilled in the art without departing from the spirit and scope of the invention, which is defined by the accompanying claims.

What is claimed is:

1. A chemical composition of Formula I:

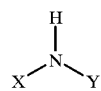

(I)

wherein:

X comprises at least one silane group; and

Y comprises a hydrocarbon backbone, at least one amide group on an α-carbon, and at least one ester group on a β-carbon with respect to N.

2. The chemical composition of claim 1, wherein Y contains only one ester group.

3. The chemical composition of claim 1, wherein Y is ethylenically saturated.

4. A chemical composition of Formula II:

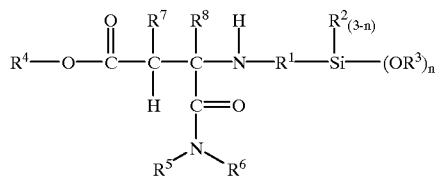

(II)

wherein:

n is 1, 2 or 3;

$R^1$ is a divalent linking group;

Each $R^2$ is independently a monovalent organic radical;

Each $R^3$ is independently a monovalent organic radical;

$R^4$ is a monovalent organic radical;

$R^5$ and $R^6$ are each independently selected from the group consisting of hydrogen and monovalent organic radicals or $R^5$ and $R^6$, when taken together, may form a 5- or 6-membered ring with the nitrogen atom;

$R^7$ is selected from the group consisting of hydrogen and monovalent organic radicals; and $R^8$ is selected from the group consisting of hydrogen and monovalent organic radicals.

5. The chemical composition of claim 4, wherein $R^1$ is selected from the group consisting of linear and branched alkylene groups having 1 to about 6 carbon atoms.

6. The chemical composition of claim 4, wherein $R^1$ is a propylene group.

7. The chemical composition of claim 4, wherein each $R^2$ is independently selected from the group consisting of linear and branched alkyl groups having 1 to about 6 carbon atoms.

8. The chemical composition of claim 4, wherein each $R^2$ is independently selected from the group consisting of a methyl group and an ethyl group.

9. The chemical composition of claim 4, wherein each $R^3$ is independently selected from the group consisting of linear and branched alkyl groups having 1 to about 6 carbon atoms.

10. The chemical composition of claim 4, wherein each $R^3$ is independently selected from the group consisting of a methyl group and an ethyl group.

11. The chemical composition of claim 4, wherein $R^4$ is an alkyl group having 1 to about 6 carbon atoms.

12. The chemical composition of claim 4, wherein $R^4$ is selected from the group consisting of a methyl group and an ethyl group.

13. The chemical composition of claim 4, wherein $R^5$ is selected from the group consisting of hydrogen and alkyl groups having 1 to about 6 carbon atoms.

14. The chemical composition of claim 4, wherein $R^5$ is hydrogen.

15. The chemical composition of claim 4, wherein $R^6$ is selected from the group consisting of an alkyl group having 1 to about 6 carbon atoms and an aryl group.

16. The chemical composition of claim 4, wherein $R^6$ is an alkyl group.

17. The chemical composition of claim 4, wherein $R^7$ is selected from the group consisting of hydrogen and alkyl groups having 1 to about 6 carbon atoms.

18. The chemical composition of claim 4, wherein $R^7$ is hydrogen.

19. The chemical composition of claim 4, wherein $R^8$ is selected from the group consisting of hydrogen and alkyl groups having 1 to about 6 carbon atoms.

20. The chemical composition of claim 4, wherein $R^8$ is hydrogen.

21. The chemical composition of claim 4, wherein n is 3.

* * * * *

UNITED STATES PATENT AND TRADEMARK OFFICE
CERTIFICATE OF CORRECTION

PATENT NO. : 6,162,938
DATED : December 19, 2000
INVENTOR(S) : Richard G. Hansen and Dean M. Moren It is certified that error appears in the above-identified patent and that said Letters Patent is hereby corrected as shown below:

Column 2,
Line 33, "U.S. Pat. No. 5,756,71" should read -- U.S. Pat. No. 5,756,751 --;

Column 12,
Line 17, after "commercially", insert -- available --;
Line 48, "Adams, CT" should read -- Adams, MA --;

Column 14,
Line 59, "ELFFEX-8" should read -- ELFTEX-8 --;

Column 18,
Line 37, "5B (0)%" should read -- 5B (0%) --;
Line 38, "5B (0)%" should read -- 5B (0%) --;
Line 46, "Prepolyme" should read -- Prepolymer --.

Signed and Sealed this

Eighteenth Day of December, 2001

Attest:

JAMES E. ROGAN
*Attesting Officer*     *Director of the United States Patent and Trademark Office*